United States Patent
Mezghani et al.

(10) Patent No.: US 11,079,581 B2
(45) Date of Patent: Aug. 3, 2021

(54) RESOLUTION PRESERVING METHODOLOGY TO GENERATE CONTINUOUS LOG SCALE RESERVOIR PERMEABILITY PROFILE FROM PETROGRAPHIC THIN SECTION IMAGES

(71) Applicant: SAUDI ARABIAN OIL COMPANY, Dhahran (SA)

(72) Inventors: Mokhles M Mezghani, Dhahran (SA); Fatai A Anifowose, Al-Khobar (SA)

(73) Assignee: SAUDI ARABIAN OIL COMPANY

( * ) Notice: Subject to any disclaimer, the term of this patent is extended or adjusted under 35 U.S.C. 154(b) by 60 days.

(21) Appl. No.: 16/694,399

(22) Filed: Nov. 25, 2019

(65) Prior Publication Data
US 2021/0157116 A1  May 27, 2021

(51) Int. Cl.
*G02B 21/00* (2006.01)
*G06T 9/00* (2006.01)
*G06T 9/40* (2006.01)

(52) U.S. Cl.
CPC .......... *G02B 21/0036* (2013.01); *G06T 9/002* (2013.01); *G06T 9/40* (2013.01); *G06T 2207/10056* (2013.01); *G06T 2207/20084* (2013.01)

(58) Field of Classification Search
None
See application file for complete search history.

(56) References Cited

U.S. PATENT DOCUMENTS

| | | | |
|---|---|---|---|
| 5,828,981 A | 10/1998 | Callender et al. | |
| 8,725,477 B2* | 5/2014 | Zhang | E21B 47/00 703/10 |
| 8,909,508 B2* | 12/2014 | Hurley | G06T 7/11 703/9 |
| 9,046,509 B2* | 6/2015 | Dvorkin | E21B 47/00 |
| 9,134,457 B2 | 9/2015 | Hurley et al. | |
| 9,142,045 B1* | 9/2015 | Cavanaugh | G06T 11/206 |
| 9,183,326 B2* | 11/2015 | de Prisco | G06F 30/20 |
| 9,187,984 B2 | 11/2015 | Usadi et al. | |

(Continued)

FOREIGN PATENT DOCUMENTS

WO  2014070572 A2  5/2014

OTHER PUBLICATIONS

Chilingarian, George V., Fu Yen, Teh , Determination of Permeability of Sandstones from Thin-Sections, Energy Sources, 8:2-3, 255-259, DOI: 10.1080/00908318608946054, 1986.

(Continued)

*Primary Examiner* — Anand P Bhatnagar
(74) *Attorney, Agent, or Firm* — Bracewell LLP; Constance Gall Rhebergen

(57) ABSTRACT

Embodiments of the present disclosure aim to provide advanced log scale permeability estimation systems and methods. In an embodiment, a computer system is provided and configured to perform petrographic thin section image permeability analysis and then generate log scale permeability estimations for a well using machine learning methods and techniques. In an embodiment, the advanced log scale permeability estimation systems and methods are configured with a computer system or a micro-computer system, that can be configured with a computer circuit board comprising a processor, memory, networking capability, and software. In another embodiment the log scale permeability estimations for a well are input into a reservoir simulation model to determine hydrocarbon resources and to make portfolio predictions for a well.

20 Claims, 6 Drawing Sheets

(56) References Cited

U.S. PATENT DOCUMENTS

| | | | |
|---|---|---|---|
| 9,201,026 B2* | 12/2015 | Walls | G01N 33/2823 |
| 9,229,127 B2 | 1/2016 | Leseur | |
| 9,507,047 B1* | 11/2016 | Dvorkin | G01V 5/101 |
| 9,747,393 B2 | 8/2017 | Dasari | |
| 10,422,736 B2* | 9/2019 | Walls | G01N 15/088 |
| 10,436,865 B2 | 10/2019 | Washburn | |
| 10,935,481 B2* | 3/2021 | Allo | G01N 33/24 |
| 2005/0206890 A1* | 9/2005 | Hurst | G06T 7/0002 |
| | | | 356/239.7 |
| 2009/0259446 A1* | 10/2009 | Zhang | G06F 30/20 |
| | | | 703/2 |
| 2012/0275658 A1* | 11/2012 | Hurley | G06T 7/11 |
| | | | 382/109 |
| 2013/0308831 A1* | 11/2013 | Dvorkin | E21B 47/00 |
| | | | 382/109 |
| 2014/0307052 A1* | 10/2014 | Ahn | G02B 21/367 |
| | | | 348/46 |
| 2016/0343150 A1* | 11/2016 | Mezghani | G02B 21/361 |
| 2017/0074772 A1* | 3/2017 | Walls | G01N 15/088 |
| 2020/0123898 A1* | 4/2020 | Zhang | G06Q 10/10 |

OTHER PUBLICATIONS

Coskun, Sefer B., Wardlaw, Norman C., Estimation of permeability from image analysis of reservoir sandstones, Journal of Petroleum Science and Engineering, vol. 10, Issue 1, pp. 1-16, 1993.

Keehm, Youngseuk, Mukerji, Tapan, and Nur, Amos, Permeability prediction from thin sections: 3D reconstruction and Lattice-Boltzmann flow simulation, Geophysical Research Letters, vol. 31, L04606, DOI:10.1029/2003GL018761, 2004.

Peng, Sheng, Hassan, Ahmed, and Loucks, Robert G., Permeability Estimation Based on Pore Characterization and Flow Modeling from Thin-Sections Image Analysis of Grain-Dominated Carbonates, Search and Discovery Article #42117, 2017.

Peng, Sheng, Hassan, Ahmed, and Loucks, Robert G., Permeability estimation based on thin-section image analysis and 2D flow modeling in grain-dominated carbonates, Marine and Petroleum Geology 77, 2016.

Saxena N., Mako G., Hofmann R., and Srisutthiyakorn N., Estimating permeability from thin sections without Reconstruction: Digital rock study of 3D properties from 2D images. Computers & Geosciences. 102, 10.1016/j.cageo.2017.02.014, 2017.

Hossain, Zakir, Relative Permeability Prediction from Image Analysis of Thin Sections, SPE paper #143606, Prepared for the SPE EUROPEC/EAGE Annual Conference and Exhibition held in Vienna, Austria, May 23-26, 2011.

Basu, T., Claverie, M., Nolan, D., Schlumberger, Lumpur, K., Yahya, K., Suleman, M., Carigall, P., Facies Analysis: Integration of core and log data using a neural network as input for reservoir modeling in Betty Field, Malaysia, The Leading Edge, vol. 23.

The International Search Report and Written Opinion for related PCT application PCT/US2020/062291 dated Nov. 25, 2020.

* cited by examiner

305

INDIVIDUAL PERMEABILITY ESTIMATION FROM CONVENTIONAL THIN SECTION ANALYSIS — 310

| DEPTH (FT) | ESTIMATED K (mD) |
|---|---|
| X100.5 | 48.9 |
| X150.7 | 5.01 |
| X500.2 | 0.006 |
| ⋮ | ⋮ |
| X999.1 | 1.62 |
| X1500.3 | 0.934 |

CORRESPONDING WIRELINE LOGS — 320

| DEPTH (FT) | GR (GAPI) | DTC (US/F) | DTS (US/F) | RHOB (G/C$^3$) | NPHI (V/V) |
|---|---|---|---|---|---|
| X100.5 | 9.83 | 25.55 | 100.12 | 2.91 | 0.11 |
| X150.7 | 8.35 | 27.88 | 99.75 | 2.97 | 0.10 |
| X500.2 | 8.57 | 35.12 | 150.22 | 2.91 | 0.08 |
| ⋮ | ⋮ | ⋮ | ⋮ | ⋮ | ⋮ |
| X999.1 | 10.63 | 40.11 | 110.77 | 2.53 | 0.25 |
| X1500.3 | 7.09 | 32.33 | 150.65 | 3.01 | 0.15 |

CALIBRATION DATABASE — 330

| DEPTH (FT) | GR (GAPI) | DTC (US/F) | DTS (US/F) | RHOB (G/C$^3$) | NPHI (V/V) | ESTIMATED K (mD) |
|---|---|---|---|---|---|---|
| X100.5 | 9.83 | 25.55 | 100.12 | 2.91 | 0.11 | 48.9 |
| X150.7 | 8.35 | 27.88 | 99.75 | 2.97 | 0.10 | 5.01 |
| X500.2 | 8.57 | 35.12 | 150.22 | 2.91 | 0.08 | 0.006 |
| ⋮ | ⋮ | ⋮ | ⋮ | ⋮ | ⋮ | ⋮ |
| X999.1 | 10.63 | 40.11 | 110.77 | 2.53 | 0.25 | 1.62 |
| X1500.3 | 7.09 | 32.33 | 150.65 | 3.01 | 0.15 | 0.934 |

TO FIG. 4B

RESOLUTION PRESERVING METHODOLOGY TO GENERATE CONTINUOUS LOG SCALE RESERVOIR PERMEABILITY PROFILE FROM PETROGRAPHIC THIN SECTION IMAGES

FIELD

Embodiments of the present disclosure relate to reservoir permeability profiles and modeling.

BACKGROUND

Core samples are collected from wells during drilling so that they can be analyzed to determine certain characteristics of rock formations for particular well sections. The core samples are often collected during drilling from what is anticipated to be the productive reservoir sections of a well. Petrographic thin section samples can then be prepared from a plug that is extracted from sections of the core samples. After the petrographic thin section samples are prepared, images are produced from the petrographic thin section samples by using a high-resolution polarizing microscope that photographs the petrographic thin section samples. Estimations of rock properties, such as permeability, can then be determined either manually or with software that processes the images by using the photographs of the petrographic thin section samples. Petrographic thin section samples can be depth tracked based on a depth location in a reservoir of the core sample they are taken from and the information associated with the analysis of the petrographic thin section sample images can be associated with a samples original depth and location in a particular well. Overall reservoir permeability estimations can also be made from analysis of petrographic thin section sample images, though these estimations often have limited accuracy and correspondingly limited usefulness. General permeability estimations for known methods and systems are considered non-representative of the reservoir due to the microscopic scale the estimations are taken from and because only few thin sections are typically analyzed for a particular well. In prior systems that are used for reservoir scale characterization, the estimations are typically up-scaled by averaging or by other statistical methods. The upscaling method usually results in the loss of the apparent heterogeneity and other properties of the reservoir. This can introduce bias and error in the consequent applications. Some examples of the limitations of the conventional permeability estimation from thin section images are as follows: (1) the results are not continuous in depth, (2) the pore-scale resolution is considered non-representative of reservoir depth locations, and (3) the utility of the estimations is limited to validating or correlating permeability prediction models at certain points.

Prior methods have utilized predicted permeability values that are taken from limited petrographic thin section images at the microscopic scale and for limited depth sections of a particular well. This data was thus limited and not in a form where it could be utilized in log scale reservoir models. As reservoir models are usually constructed at log scales, reservoir models benefit from full log scale data sets. Prior systems that utilize parameters derived from thin section images often employ two-dimensional/three-dimensional mathematical transformation algorithms to predict permeability.

These methods have estimated permeability by using the parameters (such as grain-size distribution, porosity, specific surface area, and flow modeling results) that are derived from the thin section image analysis as input to certain numerical equations such as the modified Kozeny equation or the Darcy flow model, or other analytical workflows. Referencing another methodology, others have proposed predicting permeability from thin section images by either reconstructing three-dimensional porous media from two-dimensional thin sections or building three-dimensional flow simulation models using the Lattice-Boltzmann technique. Other methods have taken mathematical expression of two-dimensional/three-dimensional models and validated the equation using the permeability simulation based on micro-CT images to estimate the permeability of a grainstone carbonate sample. Others have proposed a methodology that replaces the need for three-dimensional reconstruction of the porous media as is done with the Lattice-Boltzmann technique. The Lattice-Boltzmann technique in particular uses a two-dimensional/three-dimensional transform algorithm to relate thin section permeability to three-dimensional rock permeability using calibration parameters. Systems that have used these technologies have several known issues, including (1) the use of complex mathematical equations that can be difficult to implement, (2) the use of various assumptions go into such equations which do not apply to all situations of the system, and (3) the use of upscaling, since the permeability obtained from these technologies are not continuous in depth. As a result these previously known systems and calculations are often inaccurate in their ability to predict the actual heterogeneity of the formation.

Using these prior methodologies, the predicted permeability estimations remain at the pore scale. As a result, the utility of these estimations are considered unrepresentative of the reservoir. It is thus desirable to focus on how the estimated permeability measurements can be transformed to a continuous log data set that is usable at the log scale. Such a system can increase utility by offering improved performance in various reservoir models. A system that does not rely on analytical or two-dimensional/three-dimensional transformations would also be advantageous. In addition, a system that utilizes machine learning technology as part of the process in constructing a continuous log data set would be desirable.

SUMMARY

Embodiments of the present disclosure aim to provide an integrated approach to generate continuous reservoir rock permeability profiles at log scale from a collection of petrographic thin section images while preserving the resolution at the log scale. In certain embodiments, the system and methodology leverages the capability of machine learning technology to develop continuous reservoir rock permeability profiles at the log scale. Often, only limited core samples and thus only limited petrographic thin sections are available for a particular well. In conventional systems and methodologies, the reservoir permeability estimated from petrographic thin sections is generally considered non-representative of a rock sample at the log scale. This is due in part to the microscopic scale of permeability estimations for the petrographic thin sections being analyze. As a result, petrographic thin section permeability estimations are under-utilized in conventional systems. In conventional systems, the estimations are upscaled by simple averaging, weighted averaging, and other methods. The downside of this approach is that the upscaling process can result in the loss of vital reservoir information (such as heterogeneity) and could negatively affect the accuracy of consequent applications that the up-scaled data may be used for. The approach described applies machine learning systems and methodology to generate a log scale continuous permeability profile while preserving the resolution and avoiding the negative effects of upscaling. In embodiments, the system and methodology involves integrating the permeability estimations obtained from a set of individual petrographic thin sections with their corresponding wireline logs matched by depth to create a calibration database. In an embodiment, the database is then further analyzed and processed to train a machine learning model. In an embodiment, this system and methodology can take as inputs the wireline logs from a new or un-cored well, and the machine learning model can be applied to predict a continuous permeability log profile at the log scale. By utilizing this system and the associated methods, the utility of permeability estimations obtained from petrographic thin section analyses is greatly increased, and in embodiments, the resulting data can be further input into various models that would in turn feed into a full-field reservoir simulation model for more accurate estimation of reservoir volume.

BRIEF DESCRIPTION OF THE DRAWINGS

The foregoing aspects, features, and advantages of embodiments of the present disclosure will further be appreciated when considered with reference to the following description of embodiments and accompanying drawings. In describing embodiments of the disclosure illustrated in the appended drawings, specific terminology will be used for the sake of clarity. However, the disclosure is not intended to be limited to the specific terms used, and it is to be understood that each specific term includes equivalents that operate in a similar manner to accomplish a similar purpose.

DETAILED DESCRIPTION

Figure 1:
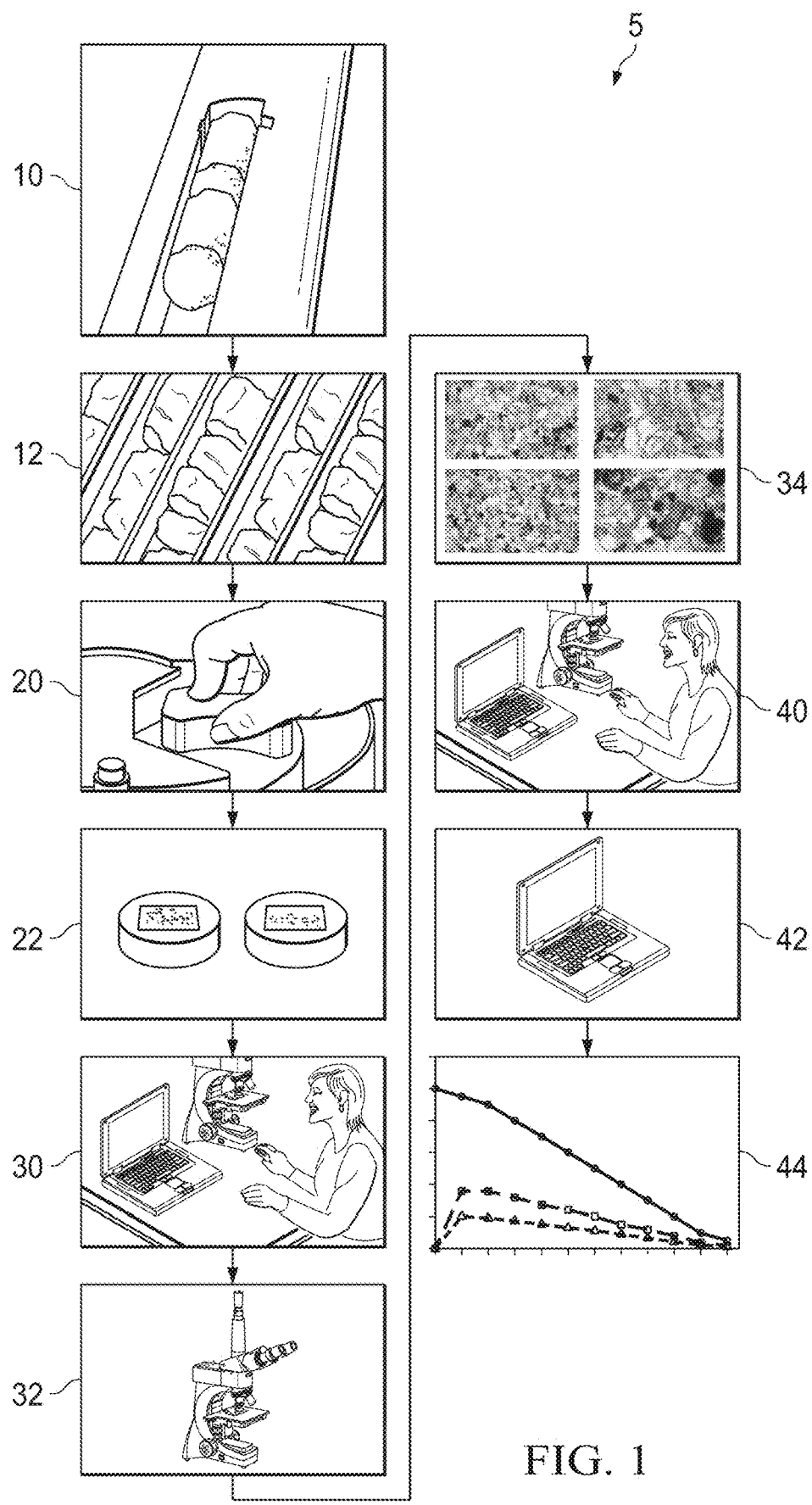
FIG. 1 illustrates a flow chart of an example core extraction through petrographic thin section sample analysis system and method.

Advantages and features of the present disclosure and methods of accomplishing the same will be apparent by referring to embodiments described in detail in connection with the accompanying drawings. The disclosed embodiments and configurations are not limited to the embodiments disclosed and may be implemented in various different forms. The embodiments are provided only for completing the disclosure and for fully representing the scope of the disclosure to those skilled in the art.

For simplicity and clarity of illustration, the drawing figures illustrate the general manner of construction, and descriptions and details of well-known features and techniques may be omitted to avoid unnecessarily obscuring the discussion of the described embodiments. Additionally, elements in the drawing figures are not necessarily drawn to scale. For example, the dimensions of some of the elements in the figures may be exaggerated relative to other elements to help improve understanding of the various example embodiments Various embodiments will be described in detail with reference to the accompanying drawings.

Embodiments of the present disclosure aim to provide integrated approach to generate continuous reservoir rock permeability profiles at log scale from a collection of petrographic thin section images while preserving the resolution at the log scale. According to an embodiment, and as illustrated in reference to FIG. 1, an example core extraction through petrographic thin section sample analysis system and method system is shown. FIG. 1. illustrates an example layout of a particular system 5 starting with the extraction of a core sample from a well. Following the step of extracting a core sample from a well 10, multiple samples are organized by the depth they were collected 12 and transported to a laboratory for further analysis. Once at the laboratory the next step is cutting core samples further into smaller plugs 20 that can be sliced into petrographic thin section samples. After the petrographic thin section samples are prepared 22, the next step is to scan the thin section samples in the laboratory 30 with a high-resolution polarizing microscope 32. In the next step, images that are representative of each petrographic thin section sample are output from the high-resolution polarizing microscope 34. A technician then loads the images into a processing program 40 on a computer system 42. The computer system utilizes specialized software that generates permeability estimations for each of the images that are representative of each petrographic thin section sample. Throughout the process the original collection depth of the core and subsequent petrographic thin section samples are tracked such that the depth information can be input into the computer system and logged along with the permeability estimations for each petrographic thin section sample. The permeability estimations for a particular well over various depths can then be graphed or turned into another visualized output 44 that is helpful for making decisions about the plan for a particular well. In an embodiment the permeability and depth information for each of the petrographic thin section samples can be stored into a database for additional analysis and processing. Other information about the samples or permeability estimates can also be stored in the database. For example, the well location, time of collection, or time of analysis, or other information may also be stored in the database and associated with a particular petrographic thin section sample.

Figure 2:
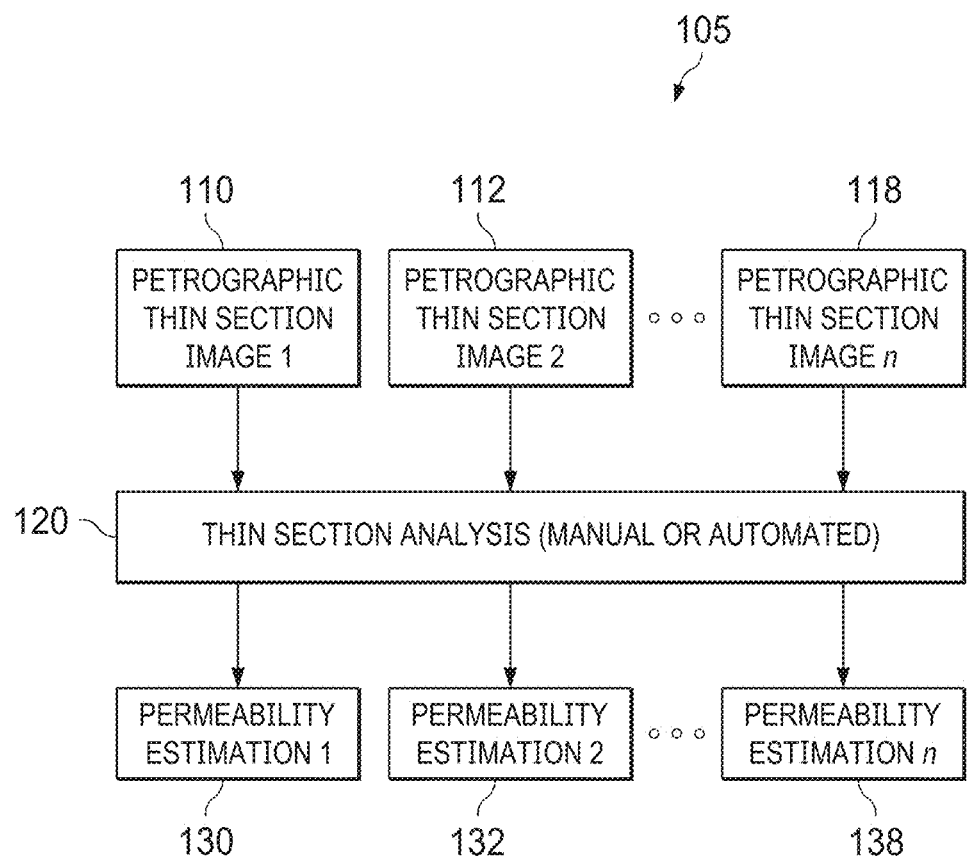
FIG. 2 illustrates a workflow example for petrographic thin section sample analysis for determining permeability estimations for multiple petrographic thin section samples.

Referring to FIG. 2, an example workflow for petrographic thin section sample analysis to determine permeability estimations for multiple petrographic thin section samples is shown 105. FIG. 2 one possible example of the petrographic thin section sample analysis portion of the process described in relation to FIG. 1. In this workflow, each of a petrographic thin section image one, petrographic thin section image two, through petrographic thin section image n undergo automated or manual thin section analysis. The thin section analysis 120 involves either manual or automated image processing on a computer system (not shown). The result of the image processing is, respectively, a permeability estimation one 130 for petrographic thin section image one 110, a permeability estimation two 132 for petrographic thin section image two 112, through a permeability estimation n 138 for petrographic thin section image n 118.

In an embodiment, the set of tools used for petrographic thin section analysis can include the thin section slides, a microscope, and image capturing software. The thin section slides can be made in the laboratory by engraving a thin film of a horizontally sliced rock sample on a glass surface. The slides are viewed under the microscope and the image capturing software is used to store a digital version of the thin section slide. In a particular embodiment, a sedimentologist looks at the digital thin section images and estimates the permeability or alternatively runs software that analyses the image and provide a permeability estimate. This value is recorded in milliDarcy (mD).

In an embodiment and specifically referring to the step of image analysis of petrographic thin section images, permeability may be estimated by using various parameters (such as grain-size distribution, porosity, specific surface area, and flow modeling results) that are derived from the thin section image analysis and input to certain numerical equations. Examples of these known equations include the Lattice-Boltzmann technique, the modified Kozeny equation and the Darcy flow model. Other known analytical workflows can also be used to estimate permeability of petrographic thin section samples. In an embodiment, other methodologies for estimating permeability can be utilized. For example, some previously known methods propose predicting permeability from thin section images by either reconstructing three-dimensional porous media from two-dimensional thin sections or building three-dimensional flow simulation models using the Lattice-Boltzmann technique. Other methods have taken mathematical expression of two-dimensional/three-dimensional models and validated the equation using the permeability simulation based on micro-CT images to estimate the permeability of a grain-stone carbonate sample. The Lattice-Boltzmann technique in particular uses a two-dimensional/three-dimensional transform algorithm to relate thin section permeability to three-dimensional rock permeability using calibration parameters. In an embodiment the computer system that receives the petrographic thin section images can be configured to perform permeability analysis using the Lattice-Boltzmann technique.

Figure 3:
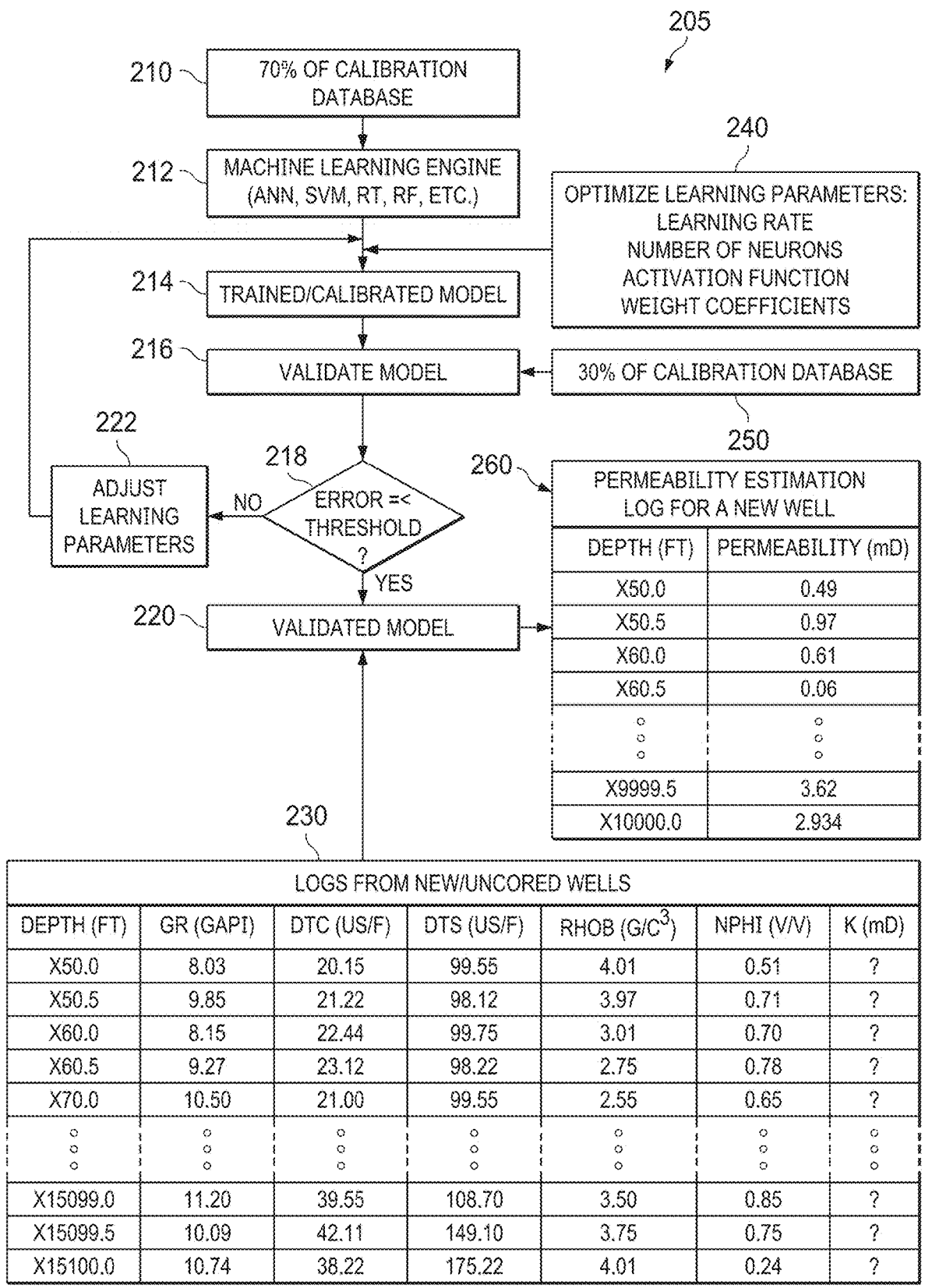
FIG. 3 illustrates a flow chart showing an example log scale permeability estimation methodology utilizing machine learning to transform petrographic thin section permeability estimations into log scale permeability estimations for a new well.

Referring to FIG. 3, a flow chart showing an example log scale permeability estimation methodology utilizing machine learning to transform petrographic thin section permeability estimations into log scale permeability estimations for a new well is shown. In an embodiment, the methodology involves integrating the permeability estimations obtained from a set of individual petrographic thin sections with their corresponding wireline logs, matching and combining each entry that has a matching depth to create a combined calibration database that includes the petrographic thin section permeability data combined with corresponding wireline logs. Again referring to FIG. 3, 70% of the calibration database is input into a machine learning engine and the other 30% of the calibration database is saved so that it can be used to verify and validate the model that will eventually result after machine learning is applied. The machine learning technique applied to the calibration database can include be any of: artificial neural network, support vector machine, radial basis function, fuzzy logic, or decision tree, or other similar machine learning techniques.

As an example of applying a machine learning technique, the steps involved in applying a typical artificial neural network application are: training, validation, and prediction. The training process can also be referred to as calibration. The data obtained from the petrographic thin section analysis results in individual data points for various different depths in a particular reservoir. In their initial form, the individual data points by themselves are generally unusable for reservoir simulation and other purposes as the individual data points are only representative of a limited sub-portion of depths for which individual petrographic thin section samples were taken and analyzed over. To perform reservoir level modeling and analysis, a log of data at a uniform depth interval (of either 0.5 feet ("ft") or 1.0 ft) is generally required. As previously described, the wireline logs corresponding to approximately the same depths are matched with those obtained from the petrographic thin section analysis to form the calibration database. Hence, in an embodiment, the calibration database is a collection of individual data points consisting of permeability values matched with their corresponding wireline logs.

The database is typically divided into two subsets: training and validation. The training subset is usually much more than the validation such as in the ratio 70:30 in which 70% go for training (as is shown being input in step 210 of FIG. 3) and the remaining 30% is used for validation (as is shown being input in step 250 of FIG. 3). In general, an embodiment, such as those described, can be configured according to the following calculations and metrics. For example, in an embodiment, the training data subset can be used to create a mathematical relationship between the wireline logs and the conventionally estimated grain sizes. This can be done by, for example, multiplying each log by a certain weight factor. The weight factor can range from 0 to +1 and is obtained from the determined degree of correlation or significance between the log and the conventionally estimated grain size. The outcome of the weighting determines the effect a particular log entry has on the overall relationship. A certain function, $f$ such as a sigmoid is used to transform the input space to a high-dimensional nonlinear space to match the nature of the subsurface data.

As an example, and in a simplified form, the follow equation may be used as part of the training methodology:

$$Y = f(a_1 X_1 + a_2 X_2 + \ldots + a_6 X_6)$$

Y is the output (grain size), $a_1 \ldots a_6$ are the weighting factors, $X_1$-$X_6$ are the logs, and $f$ is the activation function such as Gaussian or sigmoid.

A Gaussian function in the following form can be applied:

$$f(x) = e^{-x^2}$$

Where x is each of the input wireline logs. A sigmoid function in the following form can be applied:

$$f(x) = \frac{1}{1 + e^{-x}}$$

Where x is each of the input wireline logs. Parameters such as the number of layers and number of neurons in the hidden layer(s) can also be set to fit (also called tune) the equation to the calibration data.

The input part of the validation data subset is passed to the mathematical equation while keeping the output hidden. In an embodiment, the equation can be used to estimate the corresponding output to the input wireline logs. The estimated output can then be compared with the actual output kept hidden from the equation. In this example embodiment, if the residual is more than a certain threshold, the parameters are changed and the entire process is repeated. The cycle goes on until the residual is within the defined threshold. At this point, a "trained" model is determined to be ready for automated estimation of grain size for a new well.

In an embodiment, the prediction process involves porting the wireline logs for a new or uncored well to the trained model (the calibrated mathematical equation) for a new grain size estimation. Since the wireline log comes at a uniform depth interval of 0.5 ft or 1.0 ft, the estimated permeability is typically made at the same depth interval. This can be achieved without any harm to the original resolution of the point data from the petrographic thin section analysis. The validated model can then take in the new wireline log as input and generate from it a corresponding log of permeability in the same depth interval as the wireline log.

Referring again to FIG. 3, a flow chart showing an example log scale permeability estimation methodology utilizing machine learning to transform petrographic thin section permeability estimations into log scale permeability estimations for a new well 205 is shown. In an initial step, after the calibration database is assembled, 70% of the calibration database 210 is input into the machine learning engine 212. The machine learning technique applied to the calibration database can include be any of: artificial neural network, support vector machine, radial basis function, fuzzy logic, decision tree, or other similar machine learning techniques. The machine learning engine 212 then follows the previously described training or calibration steps and results in a trained/calibrated model 214. During or after the model is trained or calibrated, an optional additional step to optimize learning parameters 240 can be performed against the model. The optimize-learning-parameters step can involve adjustments to the learning rate, the number of neurons (for specific machine learning techniques such as the artificial neural network), activation function, or weight coefficients.

In an embodiment, an optional process is model re-calibration. When new or additional data (individual grain size estimation and their corresponding wireline logs) is available, it can be added to the calibration database. Then with the updated calibrated database, the same set of tuning parameters may no more be adequate to fit mathematical equation to the updated data. New sets of the tuning parameters may also be derived to establish a good fit between the updated wireline logs and the new set of grain size estimations.

Again referring to FIG. 3, after training and calibration is complete, an un-validated model is ready to be tested against the remainder of the calibration database 216. At this point the remaining unused portion of the calibration database, in this example 30% of the original calibration database 250, is input into the model to validate and verify the accuracy of the model 216. If the un-validated model is determined to be within a certain error threshold 218 it is then considered to be a validated model 220. If the un-validated model is determined to be outside of the pre-determined error threshold, adjustments can be made to the learning parameters 222 and the model is re-trained or re-calibrated with the adjusted parameters. After the model is re-trained it is run against the remainder of the calibration database for validation again and the process can repeat until the model is determined to be validated 220. Once the model is validated 220, the logs from the new/un-cored wells 230 (example data is shown in FIG. 3) can be input into the validated model. The validated model will then compare depths and other parameters to output a complete permeability estimation log for a particular well 260. In FIG. 3, the permeability estimation obtained from the validated model is shown in milliDarcy (mD).

One example of a permeability estimation by a validated model can be described as follows. First, given a trained model in the form of:

$$PERM=A*GR+B*DTC+C*DTS+D*RHOB+E*NPHI$$

where GR, DTC, DTS, RHOB, and NPHI are the input logs and A-E are the weight coefficients assigned to each log. At an example depth "X60.5", substituting for the values of the logs using the example from 230 in FIG. 3, the equation can be rewritten with the inputs inserted as:

$$PERM=A*9.27+B*23.12+C*98.22+D*2.75+E*0.78$$

In this example, if the coefficients A-E are 5.5, 3.75, 1.5, 8.01, and 11.23 respectively, inputting the respective variables and running and completing the calculation, the permeability of the rock at this depth location is calculated to be 315.8 milliDarcy (mD). This same workflow can be carried out for each depth location where the inputs and coefficients are known or may be predicted from the models.

Figure 4A:
FIGS. 4A and 4B illustrate an example data set workflow taking petrographic thin section permeability estimations and corresponding wireline logs to create a calibration data set and then using the calibration data set and machine learning to create log scale permeability estimations for the new well.
Figure 4B:
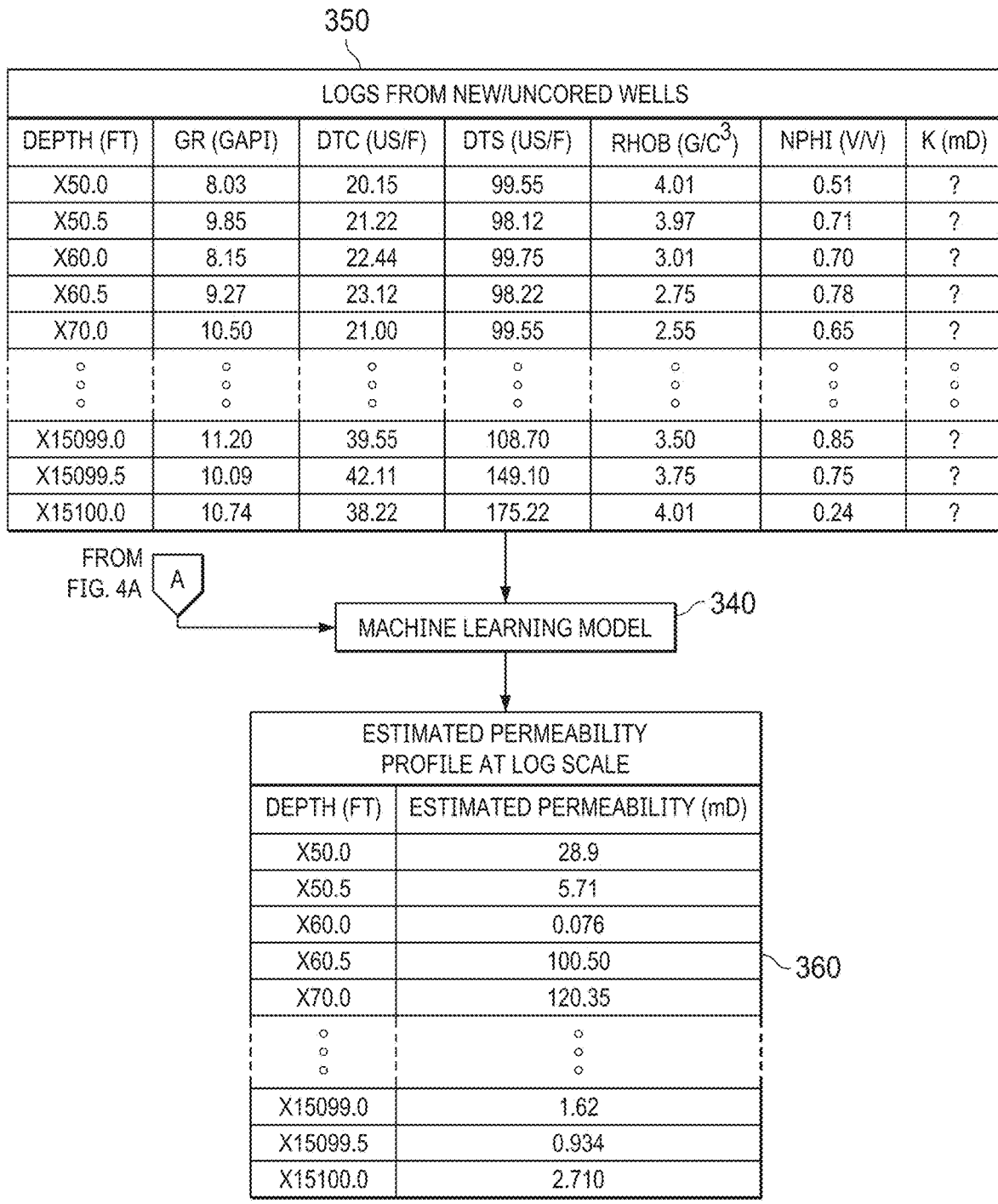

Referring to FIGS. 4A and 4B, an example data set workflow 305 taking petrographic thin section permeability estimations and corresponding wireline logs to create a calibration data set and then using the calibration data set and machine learning to create log scale permeability estimations for a new well is shown. Referring to FIG. 4A, scattered depth individual permeability estimations from conventional petrographic thin section analysis 310 is combined with wireline logs from a corresponding well 320. In an embodiment, conventional petrographic thin section analysis can refer to manual permeability estimations by known image analysis techniques or by known computer software analysis techniques. The resulting combined dataset that includes both the permeability estimations from petrographic thin section analysis and the wireline logs can be referred to as the calibration database 330. Referring to FIG. 4B, a machine learning model is generated using the system and methodology described by example with respect to FIG. 3 and the logs from new/un-cored wells that lack log scale permeability estimations 350 are input into the machine learning model 340. Similarly to the system and methodology described with respect to FIG. 3, a log scale depth based estimated permeability profile is output by the machine learning model 340. The resulting estimated permeability profile at log scale 360 can then be used for reservoir simulation or other for other similar well planning and production models.

Figure 5:
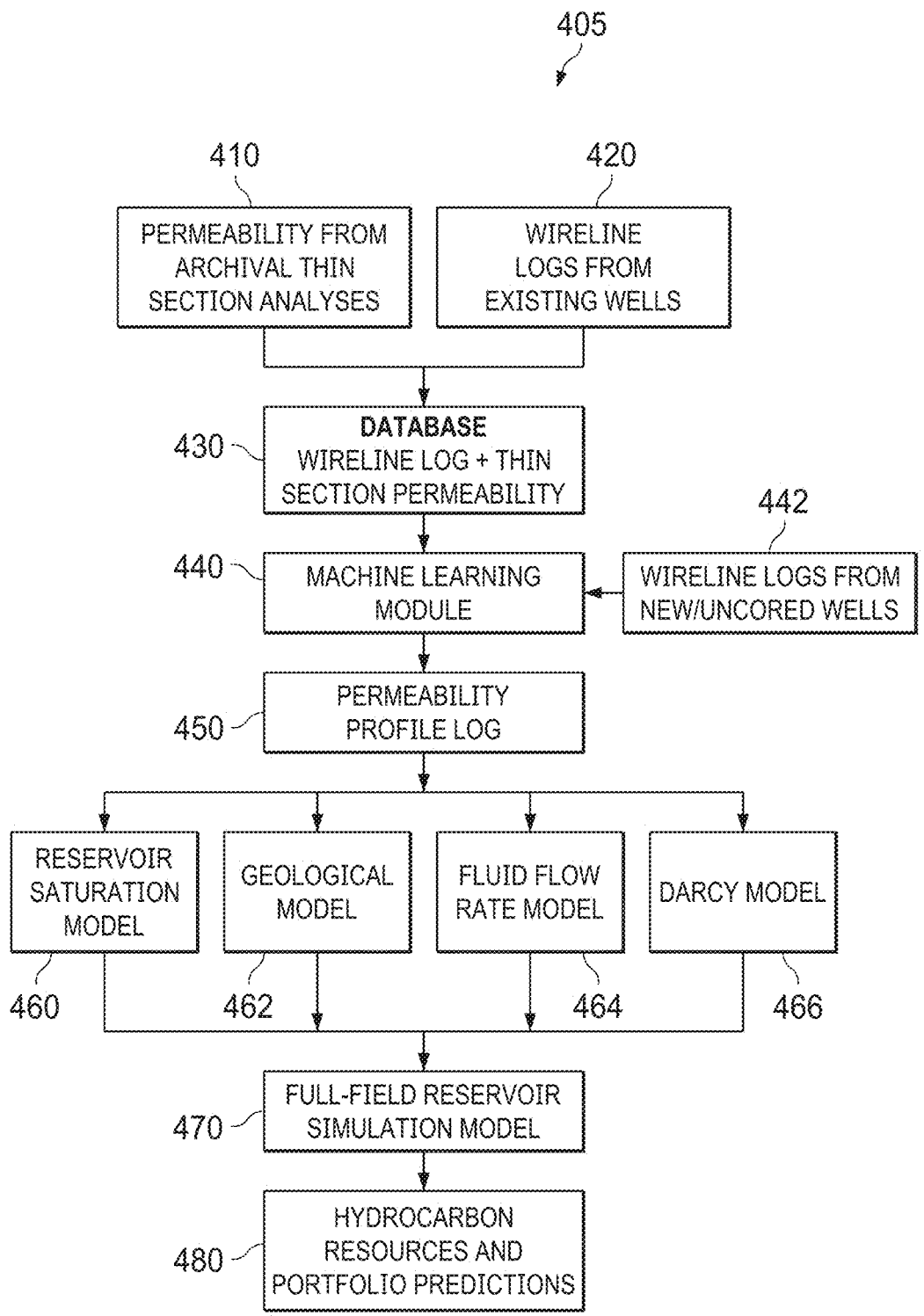
FIG. 5 illustrates an example end-to-end workflow showing example applications of the log scale permeability estimation methodology described in various reservoir simulation models to determine hydrocarbon resources and portfolio predictions.

Referring to FIG. 5, an example end-to-end workflow 405 illustrating example applications of the log scale permeability estimation methodology described in various reservoir simulation models to determine hydrocarbon resources and portfolio predictions is shown. In an embodiment, permeability from petrographic thin section analyses 410 and wireline logs from existing wells 420 are combined into a calibration database 430. A machine learning module 440 is then run against the calibration database, such as in the embodiment described with respect to FIG. 3. Once the validated model is ready, wireline logs from new/un-cored wells 442 are input to the validated model and a log scale permeability profile log is output from the validated model. The log scale permeability profile 450 can then be optionally input into various known larger scale models such as a reservoir saturation model 460, a geological model 462, a fluid flow rate model 464, a Darcy model 466, or other similar models (not shown). In an embodiment, the outputs of the various optional models can then be input into a full-field reservoir simulation model 470 that can be used to determine estimated hydrocarbon resources and make portfolio predictions for the full-field reservoir 480.

The invention claimed is:

1. An advanced log scale permeability estimation system, comprising:
   a high-resolution microscope configured to take photographs of a plurality of petrographic thin section samples and create petrographic thin section sample digital image files from the photographs, and
   a computer system configured with specialized software to perform a first specialized function and a second specialized function:
      the first specialized function to receive the petrographic thin section sample digital image files from the high-resolution microscope and analyze the petrographic thin section sample digital image files to determine a permeability estimation for each of the petrographic thin section sample digital image files and further configured to receive and store depth information associated with each of the plurality of petrographic thin section samples and the respective permeability estimation into a permeability estimation log;
      the second specialized function to combine the permeability estimation log with a set of corresponding wireline logs to form a calibration log, the computer system further configured to perform machine learning on a majority portion of the calibration log, generate a calibrated model, validate the calibrated model with a remaining portion of the calibration log, and determine if the calibrated model is within a pre-identified error threshold such that it can be considered a validated model;
   the computer system further comprising:
      a computer circuit board,
      a microprocessor configured on the computer circuit board, the microprocessor configured with input/output channels,
      memory configured to be in communication with the microprocessor,
      a data bus extending between the memory and the microprocessor, and
      a network interface configured to be in communication with the microprocessor,
      non-volatile memory configured to be in communication with the microprocessor, and
      a specialized software program stored on the nonvolatile memory that enables the microprocessor to perform each of the first specialized function and the second specialized function.

2. The system of claim 1, wherein the computer system is further configured to perform a third specialized function and the specialized software program stored on the nonvolatile memory is further configured to enable the microprocessor to perform the third specialized function, the third specialized function configured to receive logs from a new or un-cored well and process the logs using the validated model to output a log scale permeability estimation log for the new or un-cored well.

3. The system of claim 2, wherein the computer system is further configured to input the resulting log scale permeability estimation log for the new or un-cored well into a reservoir saturation model.

4. The system of claim 2, wherein the computer system is further configured to input the resulting log scale permeability estimation log for the new or un-cored well into a fluid flow rate model.

5. The system of claim 1, wherein the first specialized function of the computer system is further configured to perform the Lattice-Boltzmann technique to determine a permeability estimation for each of the petrographic thin section sample digital image files.

6. The system of claim 1, wherein the first specialized function of the computer system is further configured to perform the modified Kozeny technique to determine a permeability estimation for each of the petrographic thin section sample digital image files.

7. The system of claim 1, wherein the first specialized function of the computer system is further configured to perform the Darcy flow model technique to determine a permeability estimation for each of the petrographic thin section sample digital image files.

8. The system of claim 1, wherein the second specialized function of the computer system is further configured to perform the artificial neural network machine learning technique.

9. The system of claim 1, wherein the second specialized function of the computer system is further configured to perform the support vector machine, radial basis function, fuzzy logic, decision tree, or other similar machine learning techniques.

10. The system of claim 1, wherein the first specialized function is further configured to sort and store the permeability estimation log by depth.

11. A method of generating advanced log scale permeability estimations for a well, comprising the following steps:
    deploying an log scale permeability estimation system, comprising:
       a high-resolution microscope configured to take photographs of a plurality of petrographic thin section samples and create petrographic thin section sample digital image files from the photographs, and
       a computer system configured with specialized software to perform a first specialized function and a second specialized function:
          the first specialized function to receive the petrographic thin section sample digital image files from the high-resolution microscope and analyze the petrographic thin section sample digital image files to determine a permeability estimation for each of the petrographic thin section sample digital image files and further configured to receive and store depth information associated with each of the plurality of petrographic thin section samples and the respective permeability estimation into a permeability estimation log;
          the second specialized function to combine the permeability estimation log with a set of corresponding wireline logs to form a calibration log, the computer system further configured to perform machine learning on a majority portion of the calibration log, generate a calibrated model, validate the calibrated model with a remaining portion of the calibration log, and determine if the calibrated model is within a pre-identified error threshold such that it can be considered a validated model;

the computer system further comprising:
  a computer circuit board,
  a microprocessor configured on the computer circuit board, the microprocessor configured with input/output channels,
  memory configured to be in communication with the microprocessor,
  a data bus extending between the memory and the microprocessor, and
  a network interface configured to be in communication with the microprocessor,
  non-volatile memory configured to be in communication with the microprocessor, and
    a specialized software program stored on the non-volatile memory that enables the microprocessor to perform each of the first specialized function and the second specialized function;
the method further comprising the step of:
  performing processing steps, by the computer, system, to perform each of the first specialized function and the second specialized function.

12. The method of claim 11, wherein the computer method is further configured to perform a third specialized function and the specialized software program stored on the nonvolatile memory is further configured to enable the microprocessor to perform the third specialized function, the third specialized function configured to receive logs from a new or un-cored well and process the logs using the validated model to output a log scale permeability estimation log for the new or un-cored well.

13. The method of claim 12, wherein the computer system is further configured to input the resulting log scale permeability estimation log for the new or un-cored well into a reservoir saturation model.

14. The method of claim 12, wherein the computer system is further configured to input the resulting log scale permeability estimation log for the new or un-cored well into a fluid flow rate model.

15. The method of claim 11, wherein the first specialized function of the computer system is further configured to perform the Lattice-Boltzmann technique to determine a permeability estimation for each of the petrographic thin section sample digital image files.

16. The method of claim 11, wherein the first specialized function of the computer system is further configured to perform the modified Kozeny technique to determine a permeability estimation for each of the petrographic thin section sample digital image files.

17. The method of claim 11, wherein the first specialized function of the computer system is further configured to perform the Darcy flow model technique to determine a permeability estimation for each of the petrographic thin section sample digital image files.

18. The method of claim 11, wherein the second specialized function of the computer system is further configured to perform the artificial neural network machine learning technique.

19. The method of claim 11, wherein the second specialized function of the computer system is further configured to perform the support vector machine, radial basis function, fuzzy logic, decision tree, or other similar machine learning techniques.

20. The method of claim 11, wherein the first specialized function is further configured to sort and store the permeability estimation log by depth.

* * * * *